(12) United States Patent
Ramirez et al.

(10) Patent No.: US 8,431,554 B2
(45) Date of Patent: Apr. 30, 2013

(54) COMPOUND SHOWING ANTI-INFLAMMATORY ACTIVITY AND ANTIVIRAL ACTIVITY, PHARMACEUTICAL COMPOSITIONS COMPRISING THE SAME, A PROCESS FOR OBTAINING THE SAME AND USE OF THE SAME IN THE TREATMENT OF EPIDEMIC KERATOCONJUNCTIVITES AND HERPETIC STROMAL KERATIS

(75) Inventors: Javier Alberto Ramirez, Buenos Aires (AR); Flavia Mariana Michelini, Berazategui (AR); Lydia Raquel Galagovsky, Buenos Aires (AR); Alejandro Berra, Castelar-Prov. De Buenos Aires (AR); Laura Edith Alche, Buenos Aires (AR)

(73) Assignees: Consejo Nacional de Investigaciones Cientificas y Tecnicas (Conicet), Buenos Aires (AR); Inis Biotech LLC, Milford, DE (US)

( * ) Notice: Subject to any disclaimer, the term of this patent is extended or adjusted under 35 U.S.C. 154(b) by 412 days.

(21) Appl. No.: 12/452,575

(22) PCT Filed: Jul. 4, 2008

(86) PCT No.: PCT/IB2008/052703
§ 371 (c)(1),
(2), (4) Date: Jan. 8, 2010

(87) PCT Pub. No.: WO2009/007895
PCT Pub. Date: Jan. 15, 2009

(65) Prior Publication Data
US 2010/0120735 A1    May 13, 2010

(30) Foreign Application Priority Data
Jul. 11, 2007    (AR) ................. P070103089

(51) Int. Cl.
*A61K 31/575*    (2006.01)
*C07J 9/00*    (2006.01)
(52) U.S. Cl.
USPC .......................... 514/177; 552/546
(58) Field of Classification Search ............ 514/177; 552/546
See application file for complete search history.

(56) References Cited

U.S. PATENT DOCUMENTS

| 4,100,027 | A | 7/1978 | Weber et al. |
| 2006/0217358 | A1 | 9/2006 | Bordet et al. |
| 2007/0219173 | A1 | 9/2007 | Mangelsdorf et al. |

OTHER PUBLICATIONS

Talarico, Laura B. et al., "Structure-Activity Relationship Studies in a Set of New Brassinosteroid Derivatives Assayed Against Herpes Simplex Virus Type 1 and 2 in Cell Cultures", Medicinal Chemistry Research, 2002, pp. 434-444, vol. 11, No. 8, Birkhäuser, Boston, United States.

Jones, J. Bryan et al., "Steroids and Steroidases XX (1). Aggregation in Aqueous Solution of Steroids with Stigmastane Type C-17 Side Chains and its Influence on their Enzymic Transformations.", Steroids, 1973, pp. 525-538, vol. 22, No. 4.

Kontiza, Ioanna et al., "3-Keto steroids from the marine organisms Dendrophyllia cornigera and Cymodocea nodosa", Steroids, 2006, pp. 177-181, vol. 71, Elsevier Inc.

Tsui, P. et al., "Some Reactions of 3β-Mesyloxycholestane-5α,6β-diol and Cholest-2-ene-5α,6β-diol Acetates", Can. J. Chem., 1973, pp. 3502-3507, vol. 51.

Wachsman, Mónica B. et al., "Antiviral Activity of Natural and Synthetic Brassinosteroids", Curr. Med. Chem.—Anti-Infective Agents, 2004, pp. 163-179, vol. 3, No. 2, Bentham Science Publishers Ltd.

*Primary Examiner* — Barbara P Badio
(74) *Attorney, Agent, or Firm* — Nath, Goldberg & Meyer; Tanya E. Harkins

(57) ABSTRACT

Brassinosteriods, illustrated by the following exemplary compounds, are disclosed:

Formula IA

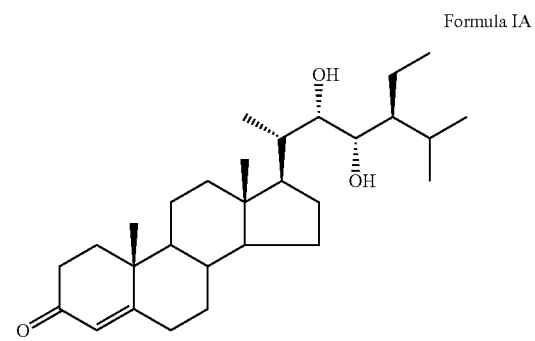

Formula IB

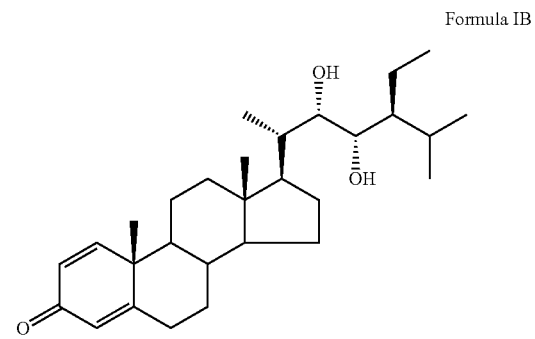

The compounds have anti-inflammatory and antiviral activity. In pharmaceutical compositions, the compounds are useful in ophthalmic pharmaceuticals for treatment of diseases caused by adenovirus, such as epidemic keratoconjunctivitis, and herpes simplex type 1, such as herpetic stromal keratitis.

13 Claims, 8 Drawing Sheets

Figure 1 A

% animals with HK

Days p.i.

Figure 1: Effect of compound I in the evolution of ocular disease induced by HSV-1 in mice treated on days 1, 2 y 3 p.i. A) incidence of HK.

Figure 1 B

Figure 1: Effect of compound I in the evolution of ocular disease induced by HSV-1 in mice treated on days 1, 2 y 3 p.i. B) severity of lesions.

Figure 2 A

% of animals with HK

Days p.i.

Figure 2: Effect of compound I in the evolution of ocular disease induced by HSV-1 in mice treated on days 6, 7 and 8 p.i.

A) incidence of HK.

Figure 2 B

*HK Severity*

*Days p.i.*

Figure 2: Effect of compound I in the evolution of ocular disease induced by HSV-1 in mice treated on days 6, 7 and 8 p.i.
B) severity of lesions.

% of inhibition of alpha-TNF production (ng/ml)
Concentration (uM)

COMPOUND SHOWING ANTI-INFLAMMATORY ACTIVITY AND ANTIVIRAL ACTIVITY, PHARMACEUTICAL COMPOSITIONS COMPRISING THE SAME, A PROCESS FOR OBTAINING THE SAME AND USE OF THE SAME IN THE TREATMENT OF EPIDEMIC KERATOCONJUNCTIVITES AND HERPETIC STROMAL KERATIS

This is a National Phase Application filed under 35 U.S.C. 371 as a national stage of PCT/IB2008/052703, filed on Jul. 4, 2008, an application claiming the benefit of Argentinean Patent Application No. P070103089, filed on Jul. 11, 2007, the content of each of which is hereby incorporated by reference in its entirety.

The present invention relates to a compound showing anti-inflammatory activity and antiviral activity according to the following structural formula:

wherein,
$R_1$ and $R_3$ are selected from H, HO—, $R_5$—O—, HCOO—, $R_5$—COO—, —OOC—$R_6$—COO—, p-toluene sulphonate, phosphate, tartrate, maleate, sulphate, fluorine, chlorine, bromine, iodine and methanesulphonate,
$R_2$ is selected from H, HO—, $R_5$—O—, HCOO—, $R_5$—COO—, —OOC—$R_6$—COO—, p-toluene sulphonate, phosphate, tartrate, maleate, sulphate, fluorine, chlorine, bromine y iodine, or —$R_1$ y —$R_2$ can be together —O—, $(CH_3)_2$—$(CO)_2$-(ó-$(CH_3$—$CH_2)_2$—$(CO)_2$—
$R_4$ and $R_5$ are selected from H and linear or branched $C_1$-$C_4$ alkyl,
$R_6$ is —$(CH_2)_n$— wherein n equals to 1, 2 ó 3, and,
can be a single bond or double bond, to the pharmaceutical compositions comprising the same, to a process for preparing the same and to the use of the same for preparing pharmaceutical compositions. Particularly, the compounds of the invention are particularly useful for preparing ophthalmic pharmaceuticals for the treatment of diseases caused by adenovirus and preferably, epidemic keratoconjunctivitis. Also, the compounds of the invention are particularly useful for preparing ophthalmic pharmaceuticals for the treatment of diseases caused by the herpes simplex type 1 (HSV-1) and preferably, herpetic STROMAL keratitis (HK).

BACKGROUND OF THE INVENTION

The adenovirus was first described as a unique antiviral agent in 1953 by Rowe et al., while attempting to establish cell cultures of tonsil and adenoid tissue. Rowe discovered that a transmissible agent was destroying the epithelial cells. Now, it is recognized that adenovirus very often cause respiratory tract diseases. However, depending on the infecting serotype, they may also cause other diseases such as for example gastroenteritis, conjunctivitis, cystitis, hepatitis and exanthema. In the case of certain serotypes, the clinical condition depends on the place of infection, for example serotype 7, acquired by inhalation, and is associated to severe lower respiratory tract diseases, while oral transmission of the same serotype causes asymptomatic infection or slight disease.

Adenoviruses are endemic in pediatric population, and it has been reported that they are the cause of up to 10% of the total infections of the respiratory tract, causing 10% of declared cases of acute gastroenteritis (Rachel Y, Moon M D. Adenovirus infections. Pediatrics in review 1999; 20:230-2).

Adenoviruses are transmitted by direct contact, by fecally-orally, by inhalation and occasionally by stagnant water. They prefer especially epithelial cells, affecting almost all mucosa. They are DNA viruses, belonging to the family Adenoviridae and genus *Mastadenovirus* (Fener F.: Classification and nomenclature of viruses. Intervirology 1976, 1-115).

Human adenoviruses are divided into 6 designed genders and classified from A to F, based on their ability to agglutination and are also subdivided into 47 serotypes, about 33% of which are related to some disease (Hierholzer J, Wigand R, Anderson L, et al. Adenoviruses from patients with AIDS: A plethora of serotypes and a description of five new serotypes. J Infect Dis 1998; 15:804-13; Horwitz M. Virology. 2nd ed New York: Reven Press: 1990)

Adenoviruses are a frequent cause of respiratory tract in infants, but many of these infections are subclinical or result in slight diseases. However, in some cases they cause severe illness (Andrew S, Day D, Mc Gregor D. Fatal adenoviral disease in siblings. Pediatr Infec Dis J 1998; 17:83-5.). The spectrum of clinical manifestations of the different serotypes of adenovirus is very broad and many times they superimpose.

Adenoviruses type 40 and 41 are an important cause of diarrhea in infants under 2 years old (Uhnoo I, Wadell G, Svensson L, et al. Importance of enteric adenoviruses 40 and 41 in acute gastroenteritis in infants and young children. J Clin Microbiol 1998; 20:365). Diarrhea and vomiting are the predominant symptoms in enteric infections by adenoviruses, as they appear in 97% and 79% of the infants respectively, with an average duration of 9 to 12 days.

The adenovirus type 7 is a recognized cause of severe disease in infants, and the effect may include chronic pulmonary disease such as bronchiectasiae and bilateral hyperlucent lung. Severe pneumonia by adenovirus has been associated to immunosupression, malnutrition or recent severe viral infection (Andrew S, Day D, Mc Gregor D. Fatal adenoviral disease in siblings. Pediatr Infec Dis J 1998; 17:83-5.).

In general, symptoms expressed by the adenovirus depend on the infecting serotype and the target affected organ/s, while its aggressiveness is inversely related to the host immunological condition.

The adenovirus can also cause acute follicular conjunctivitis. This may be the most frequent and benign adenoviral infection of the eye, it is generally unilateral and it is expressed by follicular injuries on the conjunctival surface. Symptoms are characterized by burning in the eye, sensation of a foreign matter and conjunctival erithema, resolving in a term of about 10 days to 3 weeks. An infant form of the epidemic keratoconjunctivitis has been described, affecting unweaned babies under 2 years old. Normal pseudo membranous conjunctivitis is accompanied by fever, pharingitis, otitis, diarrhea and vomiting (Mandell G, Bennett J, Dolin R.

Principles and practice of infectious disease 5$^a$ Ed, Philadelphia: Churchill Livingstone 2000.).

The epidemic keratoconjunctivitis is an infectious process of viral nature, which is characterized by affecting the conjunctiva, with secretions and infiltrations of the cornea of nummular aspect. Due to its infectious nature, there may be a tumefaction of pre-auricular lymph nodes.

As its name indicates, in the epidemic keratoconjunctivitis there is a joint affectation of the cornea and conjunctiva due to, in general, the infection by adenovirus serotype 8, 19 y 37. However, it has also been described that, though with less frequency, serotypes 2-5, 7, 9, 10, 11, 14, 16, 21 and 29 can also be the cause of this disease.

Epidemic keratoconjunctivitis is highly contagious. Preferably it affects adults that occasionally also present generalized symptoms in the form of general malaise, odynophagia and febricula. It presents a very acute onset with an important sensation of foreign matter, conjunctival and palpebral edema, mixed hyperemia and abundant tearing. All these symptoms rapidly progress and attain their maximum intensity at the third day. After the first 24 hours, follicles in the conjunctiva can be observed. Secretion, that at the beginning is waxy, turns into serofibrinous that may evolve into the formation of pseudomembranes. Between the third and fifth day, the condition bilateralizes, though contralateral affection of the eye is always slighter than in the first day. In 80% of the cases there appears superficial punctate keratitis visible with a slot lamp and after instillation of fluorocein. These lesions are resolved in a term of at least 15 days. This period is longer is subepithelial immunocomplexes are deposited, above the Bowman's layer. Thus opacificities impairing vision and that take to reabsorb a variable period of time that ranges from months to even years.

Epidemic keratoconjunctivitis uses to be a frustrating entity for the patient and physician, as so far no pharmaceutical to fight the adenovirus itself has been developed. Today, when keratoconjunctivitis is diagnosed, generally it is prescribed a symptomatic therapy based on artificial tears, lubricants and non-steroid anti-inflammatory agents, which can only improve the discomfort associated to this condition. Though corticosteroids can decrease the severe inflammation observed in some cases, they can also extend the clinical course of the disease, sometimes developing even subepithelial infiltrates.

Moreover, the infections caused by the herpes simplex virus (HSV) are widely disseminated in the human population, and this is the only natural reservoir of said virus. The herpes simplex virus type 1 (HSV-1) induces an ocular disease in humans called herpetic stromal keratitis (HK), as a consequence of an inflammatory reaction that occurs in the human eye in response to the infection (Cloaue C P M, Menage M J, Easty D L. Severe herpetic keratitis. I: Prevalence of visual impairment in clinic population. British J. Opthalmol. 1988; 72:530-33). The HK is the main cause of blindness in the industrialized countries and the first cause of cornea transplant.

Studies in animal models have been very useful to reproduce and characterize evolution of the infection induced by HSV-1, resulting in a pathology associated to the acute and recurrent disease ([Minagawa H, Sakai Y, Li Y, Ishibashi T, Inomata H and Mori R.: Suppression of infectious virus spread and corneal opacification by the combined use of recombinant interferon beta and interleukin-10 following corneal infection with herpes simplex virus-1 in mice. Antiviral Res. 1997; 36: 99-105). Thus, the murine model of ocular infection induced by HSV-1 constitutes a suitable alternative to test antiviral drugs in vivo as it allows to reproducing the man pathology (Brandt C R, Coakley L M and Grau D R. A murine model of herpes simplex virus-induced ocular disease for antiviral drug testing. J. Virol. Methods 1992; 36:209-22).

The present inventors have synthesized novel compounds that show anti-inflammatory and antiviral properties, which are especially efficient to treat diseases caused by adenoviruses and/or herpes simplex type 1. Particularly, the compounds of the present invention are particularly useful for preparing ophthalmic pharmaceuticals to treat diseases caused by adenovirus and preferably, epidemic keratoconjunctivitis. Also, particularly, the compounds of the invention are especially useful for preparing ophthalmic pharmaceuticals for the treatment of diseases caused by the herpes simplex virus type 1 (HSV-1) and preferably, herpetic stromal keratitis (HK).

BRIEF DESCRIPTION OF THE INVENTION

The present invention refers to a compound showing anti-inflammatory and antiviral activity according to the following structural formula:

wherein, $R_1$ y $R_3$ are selected from H, HO—, $R_5$—O—, HCOO—, $R_5$—COO—, —OOC—$R_6$—COO—, p-toluene sulphonate, phosphate, tartrate, maleate, sulphate, fluorine, chlorine, bromine, iodine and methanesulphonate, $R_2$ is selected from H, HO—, $R_5$—O—, HCOO—, $R_5$—COO—, —OOC—$R_6$—COO—, p-toluene sulphonate, phosphate, tartrate, maleate, sulphate, fluorine, chlorine, bromine and iodine, or —$R_1$ and —$R_2$ can be together —O—, $(CH_3)_2$—$(CO)_2$-(ó-$(CH_3$—$CH_2)_2$—$(CO)_2$—

$R_4$ and $R_5$ are selected from H y linear o branched $C_1$-$C_4$ alkyl, $R_6$ is —$(CH_2)_n$— wherein n equals to 1, 2 ó 3, and,

⚟ can be a single bond or a double bond.

In one embodiment, the invention refers to the compounds named I and II:

Compound I

Compound II

In the previous art, particularly in the presentation to the congress of Sep. 22 to 23, 2004 in the XXV Chemistry Congress (Ramirez J. A., Alvaredo M., Galagovsky L. R, Wachsman M. B. y Coto C. (Two synthetic analogues of 28-homocasterone with antiviral action in vitro, sep. 2004) the existence of a compound similar to the compound I of this invention was disclosed. However, said presentation does not contain any teaching about the anti-inflammatory properties of the same. Said presentation does not disclose the activity of this compound against adenovirus either. In fact, from the teachings of the same and, particularly, the selectivity index obtained for the antiviral activity against Herpes HSV, the skilled in the art would not be induced to study the properties of said compound against adenovirus replication. Similar conclusions are obtained upon reading Wachsman M. B. Ramirez J. A., Talarico L., Galagovsky L. R., and Coto C. E., (Antiviral activity of natural and synthetic brassinosteroids, Curr. Med. Chem., Anti-infective Agents, 2004, Vol. 3, No 2). Upon reading said publication, the skilled in the art could not infer the anti-inflammatory properties of the compounds of the invention. Also, from the results obtained, the person skilled in the art could not infer the specific properties against adenovirus that show the compounds of the invention and even less their use in pharmaceutical compositions. The skilled in the art could not possibly infer the utility of the compounds of the invention for preparing compositions for ophthalmic use to treat epidemic keratoconjunctivitis and herpetic stromal keratitis.

Moreover, in Jones J. B. and Baskevitch N. (Steroids and Steroidases XX (1) aggregation in aqueous solution of steroids with stigmastane type C-17 side chains and its its influence on their enzymic transformations, Steroids, oct 1973, pp 525-538) it is described obtaining a compound similar to the compound I of the invention, but with different stereo chemistries in C-22 and C-23. Upon reading said publication, the skilled in the art could not infer the anti-inflammatory properties and specific properties against adenoviruses of the compounds of the invention, as well as the use of the same in pharmaceutical compositions for ophthalmic use for treating epidemic keratoconjunctivitis and herpetic stromal keratitis.

DETAILED DESCRIPTION OF THE INVENTION

This invention refers to a compound showing anti-inflammatory activity and antiviral activity according to the following structural formula:

wherein, $R_1$ are $R_3$ are selected from H, HO—, $R_5$—O—, HCOO—, $R_5$—COO—, —OOC—$R_6$—COO—, p-toluene sulphonate, phosphate, tartrate, maleate, sulphate, fluorine, chlorine, bromine, iodine and methanesulphonate, $R_2$ is selected from H, HO—, $R_5$—O—, HCOO—, $R_5$—COO—, —OOC—$R_6$—COO—, p-toluene sulphonate, phosphate, tartrate, maleate, sulphate, fluorine, chlorine, bromine and iodine, or —$R_1$ and —$R_2$ can be together —O—, $(CH_3)_2$—$(CO)_2$-(ó-$(CH_3$—$CH_2)_2$—$(CO)_2$—

$R_4$ and $R_5$ are selected from H and linear or branched $C_1$-$C_4$ alkyl, $R_6$ is —$(CH_2)_n$— wherein n equals to 1, 2 ó 3, and, ⫽ can be a single bond or double bond.

In one particular embodiment, the invention refers to the compounds I and II:

Compound I

Compound II

The compounds of the invention show anti-inflammatory activity and antiviral activity and are particularly useful for inhibiting the replication of adenoviruses and herpes simplex virus type 1, which makes them especially useful for preparing pharmaceutical compositions in general and particularly ophthalmic compositions. Thus, it is a particular object of the invention an ophthalmic composition comprising at least a compound according to the abovementioned formula and pharmaceutically acceptable excipients. Preferably, the invention refers to an ophthalmic composition in liquid or semisolid form comprising at least the compound I and/or the compound II and pharmaceutically acceptable excipients.

In one particular embodiment, the invention refers to a composition of ophthalmic use for treating epidemic keratoconjunctivitis comprising one or more compounds of the invention.

It is another object of the invention a composition of ophthalmic use for treating herpetic stromal keratitis comprising one or more compounds of the invention.

Examples of solutions of ophthalmic use to be administered in the form of drops containing one or more compounds of the invention can be those in the form of aqueous or oily sterile solution, which optionally can contain anti microbial preservatives, such as benzalkonium chloride. Said solutions can be in the form of monodoses or multidoses. Preferably, those in the form of monodoses will not contain anti-microbial preservatives. Said solutions should have a viscosity of about 3-7 centistokes, a pH from about 5.8 to 7.2 and an osmolarity from about 290 to 310 mosm/kg. The skilled in the art will select the suitable excipients so that the ophthalmic solution is not toxic or irritating to the conjunctive and the cornea when it is instillated on the ocular surface. Within the scope of the invention, formulations in the form of suspension, lotion, gel, semisolid preparation, insert of ophthalmic use and intraocular application are also contemplated. The skilled in the art will select the suitable excipients so that the ophthalmic formulations are not toxic or irritating to the conjunctive and the cornea when instillated on the ocular surface. Also it is contemplated that the ophthalmic composition comprising one or more of the compounds of the invention allows the controlled release of the compounds of the invention, and particularly, that the compounds are bonded or encapsulated within the liposomes.

EXAMPLES OF THE INVENTION

Example 1

Obtaining (22S,23S)-22,23-dihydroxystigmast-4-en-3-one

In a balloon provided with a refrigerant, in an inert atmosphere, 15 grams of stigmasterol in 750 ml of toluene anhydride are dissolved. 25 ml of N-methyl-4-piperidone are added, the mixture is stirred and boiled until 50 ml of solvent are distilled.

The mixture is cooled to 60° C. and 7 grams of aluminum isopropoxide are added. The solution is refluxed during 3 hours, and taken to ambient temperature and successively washed with 200 ml of 5% aqueous hydrochloric acid, 100 ml of aqueous sodium bicarbonate and finally water.

Toluene is evaporated at reduced pressure and the resulting solid is recrystallized from methanol. 12.3 grams of (22E)-stigmast-4-en-3-one are obtained, melting point 127-128° C.

The product obtained is dissolved in a mixture consisting of 500 ml tetrahydrofuran and 100 ml water, and 1.5 grams of sodium bicarbonate, 10 mL tert-butanol, 2.8 grams of methanesulphonamide and 150 mg osmium tetroxide are added.

The resulting solution is heated to 50° C. during 24 hours and taken to ambient temperature. 12 grams of sodium bisulphate dissolved in 100 ml water are added.

The volume of solvent is reduced to reduced pressure to about 300 mL. The mixture obtained is extracted 3 times with 100 mL of ethyl acetate. The organic extract is dried with sodium sulphate anhydrous and evaporated to dryness at reduced pressure.

The crude product is purified by silica column chromatography (eluting solvent: hexane/ethyl acetate 1:1). 8.9 grams of (22S,23S)-22,23-dihydroxystigmast-4-en-3-one are obtained.

$^1$H-RMN (CDCl$_3$, 200 MHz): 5.72 (1H, s, H-4); 3.61 (2H, m, H-22 y H-23).

$^{13}$C-RMN (CDCl$_3$, 50 MHz): 198.4 (C-3); 170.4 (C-5); 123.9 (C-4); 72.3 (C-22); 70.7 (C-23).

IR: 3300 y 1680 cm$^{-1}$.

Example 2

Obtaining (22S,23S)-22,23-dihydroxycholest-4-en-3-one

Following a procedure similar to the one described in Example 1, but using 100 mg 22-dehydrocholesterol as starting steroid, 48 milligrams of (22S,23S)-22,23-dihydroxycholest-4-en-3-one are obtained.

$^1$H-RMN (CDCl$_3$, 200 MHz): 5.72 (1H, s, H-4); 3.69 (2H, m, H-22 y H-23).

$^{13}$C-RMN (CDCl$_3$, 50 MHz): 198.4 (C-3); 170.4 (C-5); 123.9 (C-4); 71.9 (C-22); 70.5 (C-23).

IR: 3300 y 1680 cm$^{-1}$.

Example 3

Obtaining (22S,23S)-22,23-dihydroxyergost-4-en-3-one

Following a procedure similar to the one described in Example 1, but using 200 milligrams of brassicasterol as starting steroid, 105 milligrams of (22S,23S)-22,23-dihydroxyergost-4-en-3-one are obtained.

$^1$H-RMN (CDCl$_3$, 200 MHz): 5.72 (1H, s, H-4); 3.79 (2H, m, H-22 and H-23).

$^{13}$C-RMN (CDCl$_3$, 50 MHz): 198.4 (C-3); 170.4 (C-5); 123.9 (C-4); 72.1 (C-22); 71.0 (C-23).

IR: 3300 y 1680 cm$^{-1}$.

Example 4

Obtaining (22R,23S)-22,23-dihydroxystigmast-4-en-3-one y (22R,23S)-22,23-dihydroxystigmast-4-en-3-one 5 g of (22E)-stigmasta-4,22-dien-3-one are dissolved in 30 mL of methylene chloride containing 2.48 g metachloroperbenzoic. The mixture is kept in darkness for six days at ambient temperature. Then, 300 ml of methylene chloride are added and the solution is washed with 10% potassium carbonate in water and then with water; it is dried over magnesium sulphate and methylene chloride evaporated. The solid residue (about 6 g) contains about 40% of the starting product that can be separated from the desired product by silica column chromatography with toluene/ethyl ether (9:1) as eluting solvent. The product, 22,23-epoxystigmast-4-en-3-one, is obtained as a mixture of diastereomers, that can be separated by crystallization of the methanol fraction. From one gram of the mixture, two diastereomers can be separated, (22R,23S)-22,23-epoxystigmast-4-en-3-one, with a melting point of 111-112° C. and (22S,23R)-22,23-epoxystigmast-4-en-3-one with a melting point of 138-140° C. (literature reports 117-118 for the mixture of both: Morita K, Iwama T, Kamano Y, Nippon Kagakukai 36, 1332 (1963); Morugita K, Yamano Y and Iwama T, ibid, 36, 1337 (1963).) 900 milligrams of the isomer epoxies are dissolved in 30 mL tetrahydrofuran and 1.1 mL of perchloric acid are added. The solution is stirred during two days at ambient temperature. The reaction mixture is diluted with ether (250 mL), then washed with water; dried over magnesium sulphate and evaporated. Purification is performed by column chromatography, with toluene ether (9:1), obtaining the mixture of diastereomer diols (750 mg). Another chromatographic purification with the same solvent, followed by acetone recrystallization gives 320 mg of (22R,23S)-22,23-dihydroxystigmast-4-en-3-one, melting point 209-211° C. $^1$H-RMN (CDCl$_3$, 200 MHz): 5.72 (1H, s, H-4); 3.80 (2H, m, H-22 y H-23).

$^{13}$C-RMN (CDCl$_3$, 50 MHz): 198.4 (C-3); 170.4 (C-5); 123.9 (C-4); 72.3 (C-22); 70.7 (C-23).

IR: 3300 and 1680 cm$^{-1}$.

Subsequent elution allows obtaining 280 mg of (22R,23S)-22,23-dihydroxystigmast-4-en-3-one, melting point 192-194° C.

$^1$H-RMN (CDCl$_3$, 200 MHz): 5.72 (1H, s, H-4); 3.79 (2H, dd, J=8 Hz and 3 Hz, H-22 and H-23)

$^{13}$C-RMN (CDCl$_3$, 50 MHz): 198.4 (C-3); 170.4 (C-5); 123.9 (C-4); 72.3 (C-22); 70.7 (C-23).

IR: 3300 and 1680 cm$^{-1}$

Example 5

Obtaining (22S,23S)-22,23-dihydroxystigmast-4-en-3-one and (22R,23R)-22,23-dihydroxystigmast-4-en-3-one 420 mg of (22E)-stigmasta-4,22-dien-3-one are dissolved in 100 mL of tert-butanol and the same volume of water is added. To this mixture 0.93 g of the chiral auxiliary DHQD$_2$-Phal, 450 mg (2 mmol) methanesulphonamide, 4.5 g of potassium ferricianide, 2 g of potassium carbonate and 30 mg de potassium osmate are added. The mixture is vigorously stirred, at ambient temperature, during 9 days. The reaction, controlled by thin layer chromatography is not completed. Little portions of solid sodium bisulphate are added, until bubbling stops. The mixture is extracted with ethyl acetate, washed with 0.25M aqueous sulphuric acid, then with 10% NaOH 10%, and finally with water. The organic phase is dried and evaporated. The crude product is purified by column chromatography (eluting solvent: hexane/ethyl acetate 1:1). 180 mg of (22S,23S)-22,23-dihydroxystigmast-4-en-3-one are obtained, subsequently 165 mg of (22R,23R)-22,23-dihydroxystigmast-4-en-3-one are eluted.

$^1$H-RMN (CDCl$_3$, 200 MHz): 5.72 (1H, s, H-4); 3.72 (1H, d, J=9 Hz, H-23); 3.58 (1H, d, J=9 Hz, H-22).

$^{13}$C-RMN (CDCl$_3$, 50 MHz): 198.4 (C-3); 170.4 (C-5); 123.9 (C-4); 74.5 (C-22); 72.6 (C-23).

IR: 3300 and 1680 cm$^{-1}$

Example 6

Obtaining (22S,23S)-22,23-dihydroxystigmasta-1,4-dien-3-one 120 mg of (22S,23S)-22,23-dihydroxystigmast-4-en-3-one are dissolved in 15 mL dioxane anhydrous. 180 mg of 2,3-dichlorine-5,6-diciano-1,4-benzoquinone (DDQ) are added and the mixture is refluxed, with stirring and inert atmosphere, during 24 hours.

The resulting suspension is filtrated and the filtrate evaporated to dryness. The resulting crude product is purified by silica column chromatography (eluting solvent: hexane/ethyl acetate 1:1). 87 mg of (22S,23S)-22,23-dihydroxystigmasta-1,4-dien-3-one are obtained.

$^1$H-RMN (CDCl$_3$, 200 MHz): 6.50 (1H, d, J=10 Hz, H-1); 5.93 (1H, d, J=10 Hz, H-2); 5.80 (1H, s, H-4); 3.61 (2H, m, H-22 and H-23)

$^{13}$C-RMN (CDCl$_3$, 50 MHz): 186.0 (C-3); 168.4 (C-5); 155.3 (C-1); 127.4 (C-2); 123.8 (C-4); 72.3 (C-22); 70.7 (C-23).

IR: 3300 and 1665 cm$^{-1}$

Example 7

Obtaining (22S,23S)-22,23-dihydroxy-6α-fluorostigmast-4-en-3-one 220 mg of (22E)-stigmast-4-en-3-one are dissolved in 50 mL ethyl acetate anhydrous. 0.35 mL acetic anhydride and 0.05 mL 70% aqueous perchloric acid are added. The solution is stirred in an inert atmosphere during 2 hours, and subsequently washed three times with 50 mL of water, then with 50 mL of 10% sodium bicarbonate solution and finally with 50 mL of water. The organic phase is dried and evaporated to dryness. The obtained enol acetate is dissolved, without previous purification, in 50 mL of acetonitrile anhydrous.

To this solution 320 mg of N-fluoro pyridinium are added, and the resulting mixture is refluxed under argon atmosphere during 18 hours.

Upon completion of the reaction the solvent is evaporated, and the crude product is purified by silica column chromatography (eluting solvent: hexane/ethyl acetate 8:2). 170 mg of 6α-fluorineostigmast-4-en-3-one were obtained.

$^1$H-RMN (CDCl$_3$, 200 MHz): 6.02 (1H, s, H-4); 5.15 (2H, m, H-22 and H-23); 5.02 (1H, double multiplet, J=42 Hz, H-6).

$^{13}$C-RMN (CDCl$_3$, 50 MHz): 199.2 (d, J=3 Hz, C-3); 166.0 (d, J=35 Hz, C-5); 129.1 (d, J=11 Hz, C-4); 137.7 (C-22); 129.8 (C-23).

IR: 3300 and 1680 cm$^{-1}$

The double bond of the lateral chain of the previous compound is dehydroxylated similarly as the Example 1, obtaining 120 mg of (22S,23S)-22,23-dihydroxy-6α-fluorostigmast-4-en-3-one.

$^1$H-RMN (CDCl$_3$, 200 MHz): 6.02 (1H, s, H-4); 5.02 (1H, double multiplet, J=42 Hz, H-6); 3.61 (2H, m, H-22 y H-23)

$^{13}$C-RMN (CDCl$_3$, 50 MHz): 199.2 (d, J=3 Hz, C-3); 166.0 (d, J=35 Hz, C-5); 129.1 (d, J=11 Hz, C-4); 72.1 (C-22); 70.6 (C-23).

IR: 3300 and 1655 cm$^{-1}$

Example 8

Obtaining (22S,23S)-22,23-dihydroxy-6α-fluorostigmasta-1,4-dien-3-one 70 mg of (22S,23S)-22,23-dihydroxy-6α-fluorostigmast-4-en-3-one are treated with DDQ following the procedure described in the Example 6. After purification by silica column chromatography (eluting solvent: hexane/ethyl acetate 8:2) of the obtained crude product, 35 mg of (22S,23S)-22,23-dihydroxy-6α-fluorostigmasta-1,4-dien-3-one are obtained.

$^1$H-RMN (CDCl$_3$, 200 MHz): 7.50 (1H, d, J=10 Hz, H-1); 6.59 (1H, d, J=10 Hz, H-2); 6.45 (1H, s, H-4); 5.15 (1H, double multiplet, J=42 Hz, H-6); 3.61 (2H, m, H-22 y H-23).

$^{13}$C-RMN (CDCl$_3$, 50 MHz): 199.2 (d, J=3 Hz, C-3); 166.0 (d, J=35 Hz, C-5); 155.3 (C-1); 129.1 (d, J=11 Hz, C-4); 127.4 (C-2); 72.1 (C-22); 70.6 (C-23).

IR: 3300 and 1655 cm$^{-1}$

Example 9

Obtaining (22S,23S)-6α,22,23-trihydroxystigmast-4-en-3-one 100 mg of (22S,23S)-22,23-dihydroxystigmast-4-en-3-one are dissolved in 15 mL dichloromethane anhydrous. 55 mg of selenium dioxide are added and the mixture is stirred in an inert atmosphere, during 8 hours.

The resulting suspension is filtrated and the filtrate is evaporated to dryness. The resulting crude product is purified by silica column chromatography (eluting solvent: hexane/ethyl acetate 1:2). 87 mg of (22S,23S)-6α,22,23-trihydroxystigmast-4-en-3-one are obtained.

$^1$H-RMN (CDCl$_3$, 200 MHz): 5.83 (1H, s, H-4); 4.57 (1H, m, H-6); 3.61 (2H, m, H-22 and H-23)

$^{13}$C-RMN (CDCl$_3$, 50 MHz): 200.1 (C-3); 168.3 (C-5); 126.0 (C-4); 72.3 (C-6); 72.3 (C-22); 70.7 (C-23).

IR: 3300 and 1680 cm$^{-1}$

Example 10

Obtaining (22S,23S)-6α,22,23-trihydroxy stigmasta-1,4-dien-3-one 50 mg of (22S,23S)-6α,22,23-trihydroxystigmast-4-en-3-one are treated with DDQ following the procedure described in Example 6. After purification by silica column chromatography (eluting solvent: hexane/ethyl acetate 8:2) of the crude product obtained, 35 mg of (22S,23S)-6α,22,23-trihydroxystigmasta-1,4-dien-3-one are isolated.

$^1$H-RMN (CDCl$_3$, 200 MHz): 7.02 (1H, d, J=10 Hz, H-1); 6.34 (1H, s, H-4); 6.21 (1H, d, J=10 Hz, H-2); 4.49 (1H, m, H-6); 3.61 (2H, m, H-22 y H-23).

$^{13}$C-RMN (CDCl$_3$, 50 MHz): 187.3 (C-3); 161.5 (C-5); 154.6 (C-1); 129.5 (C-2); 125.5 (C-4); 72.3 (C-22); 70.7 (C-23); 67.7 (C-6).

IR: 3300 and 1680 cm$^{-1}$

Example 11

Evaluation of Antiviral Activity In Vitro of the Compounds I and II

The activity anti-HSV-1 of the compounds I and II was evaluated in human conjunctive cells (IOBA-NHC). First, it was determined cytotoxicity of the same for cells IOBA-NHC using the colorimetric assay with MTT, based on the cleavage of the tetrazolium salt MTT (3-(4,5-dimethylthiazol-2-yl)-2,5-diphenyl tetrazolium bromine) by the mitochondrial enzyme succinate dehydrogenase, to obtain a blue product, formazan (Denizot F, Lang R. Rapid colorimetric assay for cell growth and survival. Journal of Immunological Methods 1986; 89:271-77). The compounds dissolved in ethanol are added to confluent monolayers of cells IOBA-NHC grown in microplates of 96 wells, in concentrations of up to 600 µM, according to the compound. The ethanol concentration was lower than 1%. After 24 hours of incubation at 37° C., the absorbency of each well was read at 570 nm, with a reference wave length of 630 nm. It was determined the 50% cytotoxyc concentration (CC$_{50}$) as the concentration of compound that reduces absorbency to 50% in relation with the control not treated (Table 1).

To evaluate the antiviral activity of the compounds I and II, monolayers of cells IOBA-NHC grown in microplates of 24 wells were infected with the strain KOS of HSV-1 at a multiplicity of infection (m.i.) of 0.2, and treated with different concentrations of the compounds. Infected cells not treated were used as control of the infection. After incubating at 37° C. during 24 h, the free and cell associated virus was harvested and titrated in Vero cells by plating in semisolid medium. It was observed an inhibition of dose-dependent viral replication in the cells treated with the compounds I and II (Table 1).

TABLE 1

Cytotoxicity and anti-HSV-1 activity of the compounds I and II

|  | I | II |
|---|---|---|
| CC$_{50}$ (µM) [a] | 71.2 | 70.8 |
| CE$_{50}$ (µM) [b] | 5.4 | 17.9 |
| IS [c] | 13.2 | 3.9 |

[a] Cytotoxyc concentration 50
[b] Effective concentration 50
[c] Selectivity index (CC$_{50}$/CE$_{50}$)

Results show that the compounds I and II have anti-HSV-1 activity and, particularly, that compound I is more active than II, as the latter shows a higher selectivity index.

Example 12

Study In Vivo about the Antiviral and/or Anti-Inflammatory Activity of the Compound I in a Murine Model of Herpetic Stromal Keratitis (HK)

Considering the anti-HSV-1 activity of compound I in conjunctival tissue cells, it was decided to evaluate its ability to cure HK in an experimental murine model.

A toxicity assay in vivo was performed. By daily observation groups of 5 mice that were treated with compound I, three times a day, during three consecutive days, it was confirmed the absence of toxic effects at a concentration of 40 μM.

To determine if the treatment with compound I, after viral inoculation, affected the signs of HK, male mice of 6-8 weeks were anesthetized with ketamine/xylazine intraperitoneally and infected with the strain KOS of HSV-1 in the right corneas, previously scrapped with a needle. One group of animals was treated with buffered saline solution (PBS) (control of disease), while the rest were treated topically with a concentration of 40 μM of compound I three times a day. Also, groups of animals to control the antiviral activity of aciclovir (ACV) and anti-inflammatory activity of dexamethasone (DEX) were included, both drugs were commercially available.

It was determined the incidence of the disease as well as the degree of severity of the lesions and evolution of HK was determined under a magnifying glass during 15 days. The diagnosis of the disease is based on the density of inflammatory infiltrates, lengthening of vessels with corneal invasion (neovascularization), and the presence of surface ulcers. Therefore, mice presenting swollen eyelids (blepharitis), neovascularization in more than 10% of the corneal surface, and corneal opacity with or without signs of necrosis, were considered sick of HK.

Figure 1:
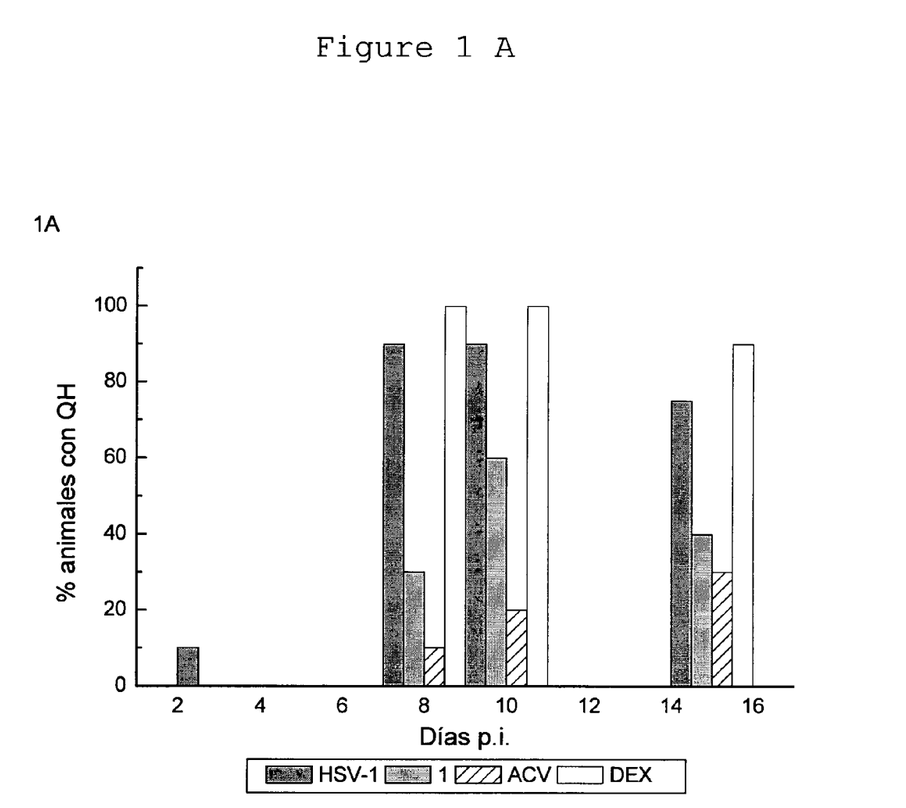
FIG. 1A shows the effect of compound I in the evolution of ocular disease induced by HSV-1 in mice subsequently treated on days 1, 2 and 3, and the incidence of post infection herpetic stromal keratosis.
FIG. 1B shows the effect of compound I in the evolution of ocular disease induced by HSV-1 in mice subsequently treated on days 1, 2 and 3, and the severity of lesions post infection.
Figure 2:
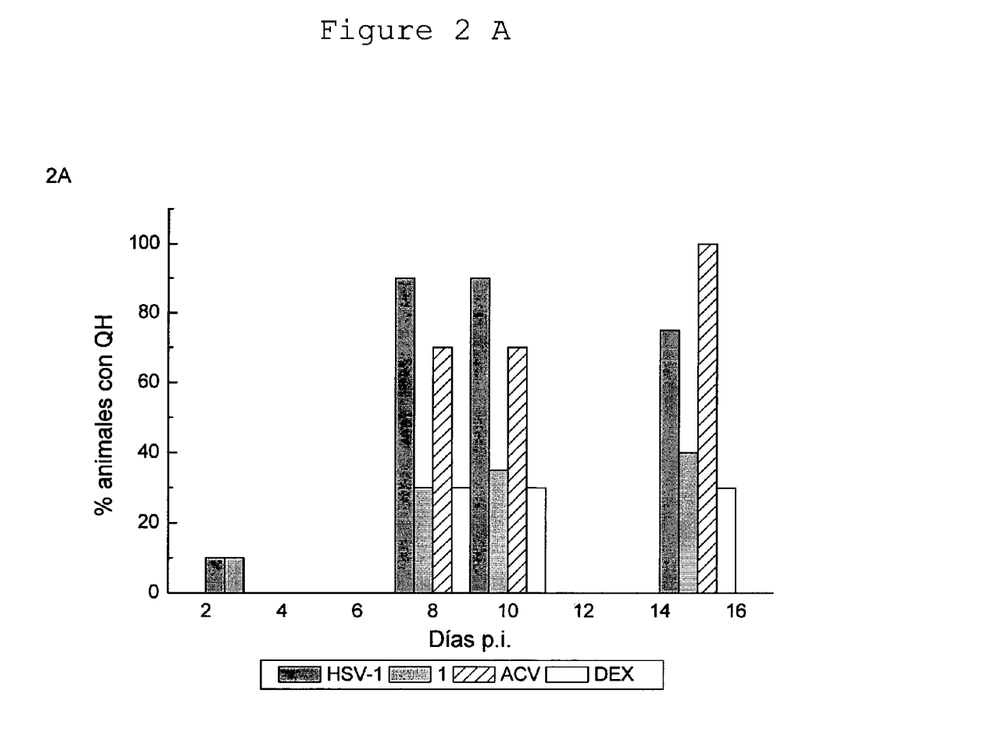
FIG. 2A shows the effect of compound I in the evolution of ocular disease induced by HSV-1 in mice subsequently treated on days 7, 8 and 9, and the post infection incidence of herpetic stromal keratosis.
FIG. 2B shows the effect of compound I in the evolution of ocular disease induced by HSV-1 in mice subsequently treated on days 7, 8 and 9, and the severity of lesions post infection.

The signs of ocular signs are gradually developed from the days 6-7 post-infection (p.i.) and the percentage of animals with HK and severity of the signs of the disease on days 3, 8, and 15 p.i were recorded (FIG. 1 y 2).

To evaluate the antiviral activity of compound I, the compound was applied to a group of animals on days 1, 2 y 3 p.i., the days when multiplication of HSV-1 in the cornea occurs. Also, other groups of mice were treated with ACV—as a positive control of antiviral activity—and with DEX.

90% of the non-treated infected mice showed keratitis lesions on day 8 p.i., while only 30% of the mice treated with the compound I showed signs of keratitis on day 8 p.i., while 10% of the animals treated with ACV were sick (FIG. 1A). All the mice treated with DEX got HK (FIG. 1A). Upon completion of the period of disease, the incidence of HK on the animals treated with compound I or ACV resulted similar (40 y 30%, respectively) (FIG. 1A). The level of damage was correlated to the incidence of HK, finding significant differences between the severity of lesions corresponding to non-treated infected mice and the animals infected and treated with ACV as well as with compound I (FIG. 1B).

To evaluate the anti-inflammatory activity of compound I, the compound was applied on days 6, 7 and 8 p.i., the time when HK manifests.

The HK signs were reduced significantly in the group treated with compound I from day 6 p.i., compared to non-treated animals, as only 30% of the mice presented signs of the disease on day 8 p.i. and 40% on day 10 p.i. (FIG. 2A). Said percentages resulted similar in the case of the treatment with an anti-inflammatory as DEX, while, as expected, the ACV had no effect on the improvement of disease signs (FIG. 2A). Also, the severity of the signs of keratitis was lower on the animals treated with compound I and DEX compared to the infection control al corresponding treatment with ACV (FIG. 2B).

Conclusions

The synthetic compounds named compounds I and II maintain the structure which is attributed the antiviral activity (side chain) and incorporate similar structures to certain steroids with known anti-inflammatory activity. Said compounds have shown to be effective in the treatment of murine HK. Both compounds presented antiviral activity in vitro (Table 1). To perform the assays in vivo, compound I was selected as it shows a higher selectivity index, which means that it is more active than compound II (Table 1).

The compound I improved the clinical signs and severity of the lesions of HK when administered on day 6 p.i. (FIG. 2) and, consequently, said compound prevented stromal inflammation mediated by the immune response. Compound I retains the dehydroxylated side chain of brassinosteroids, and has the rings A and B of the cortisone in its structure. Adding group ceto in 3 and the double bond 4-5 confers to the molecule an anti-inflammatory activity in vivo similar to dexamethasone. This is observed in the treatment of HK after topication of animals once lesions appeared. Also, compound I has the additional benefit of improving the disease when added on the first 3 days p.i. as well as ACV (FIG. 1), while dexamethasone favors a higher viral replication and exacerbation of HK signs.

Therefore, it is thus evidenced that the present invention provides new compounds effective in the treatment of HK, which have antiviral as well as anti-inflammatory activity.

Example 13

Study In Vitro of Antiviral and/or Anti-Inflammatory Activity of Compound I when Applied to a Normal Human Conjunctive Epithelium Cell Line (IOBA-NHC) Infected with Adenovirus (ADV-5)

Figure 3:
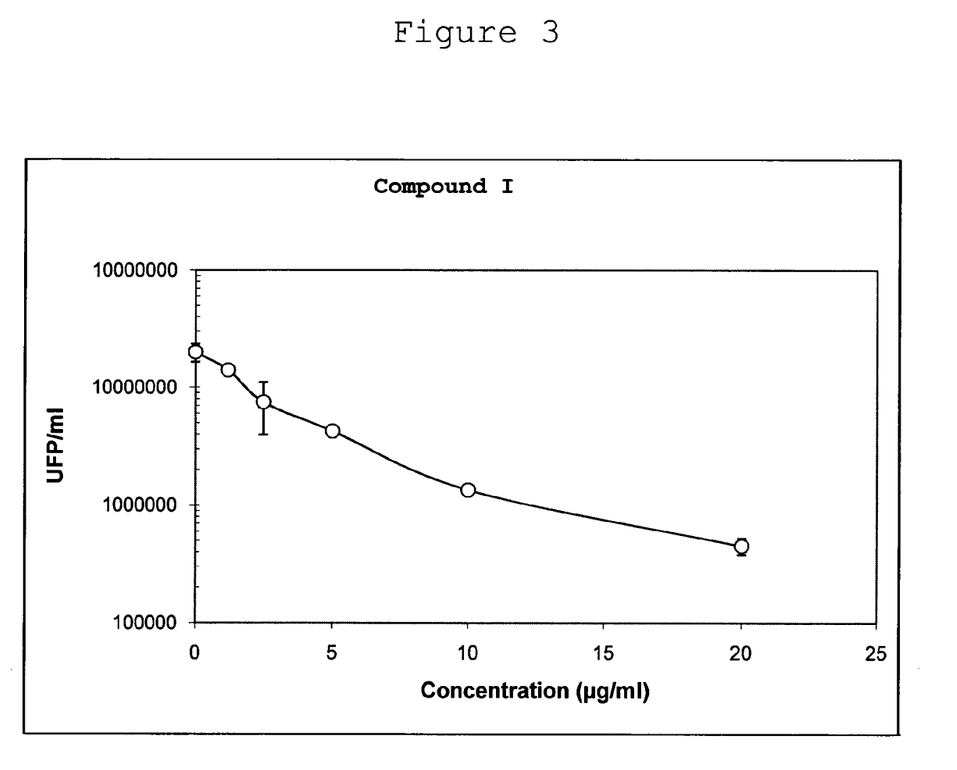
FIG. 3 shows the antiviral activity of compound I according to the concentration used against adenovirus in cultures of normal human conjunctive epithelium cell line infected with adenovirus (ADV-5).

The compound I shows antiviral activity against adenovirus. By cultures of a normal human conjunctive epithelium cell line designated IOBA-NHC, infected with adenovirus (ADV-5), at a multiplicity of infection of 1 and treated with different concentrations of compound I, the inventors of this invention have been able to show that said compound inhibits virus replication according to the concentration of compound used (FIG. 3).

The antiviral selectivity index of Compound I for adenovirus is of 31.6. Said index was determined as a quotient between its viral activity ($=63.2$) and its cytotoxicity ($=2$).

Figure 4:
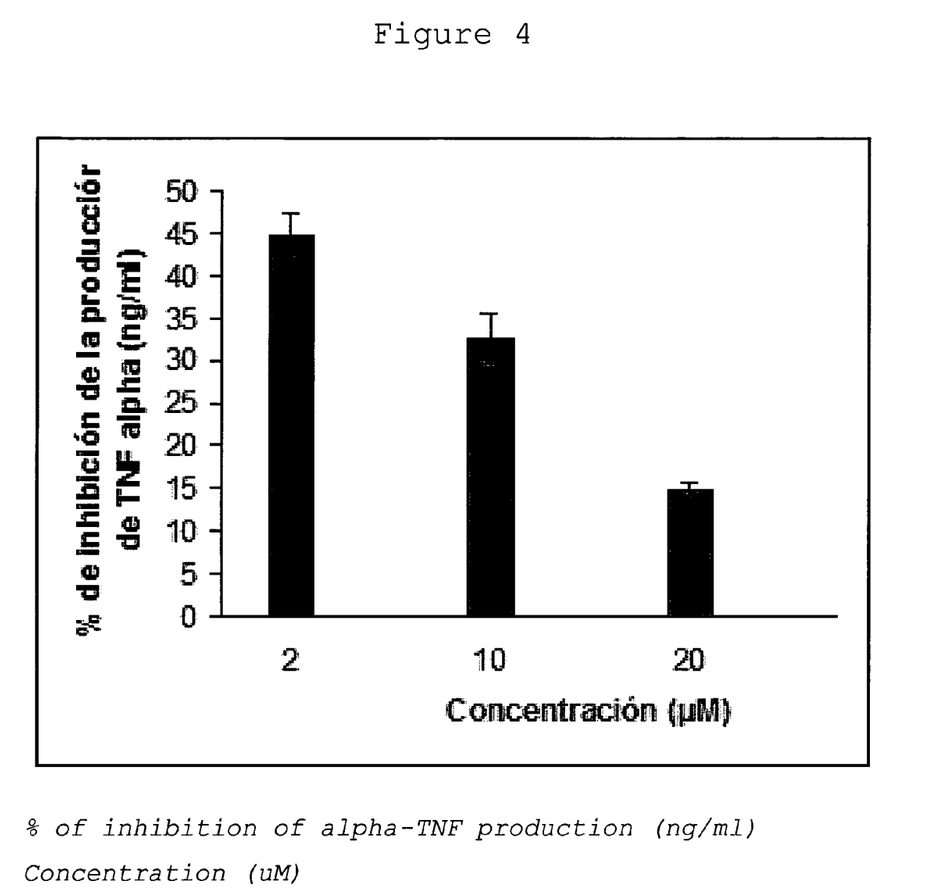
FIG. 4 shows the anti-inflammatory activity of compound I at different concentrations as demonstrated by percentage of inhibition of alpha-TNF production n macrophages.

Also, compound I has anti-inflammatory activity. By cultures of a cell line of inflammatory cells (macrophages) designated J774, treated with an agent that produces inflammation (LPS) and different concentrations of Compound I, the inventors of this invention have been able to show that said compound inhibits production of alpha-TNF in cultures of said cell line. Data evidencing said conclusion are shown in FIG. 4.

Example 14

Study In Vitro of Antiviral and/or Anti-Inflammatory Activity of Compound II when Applied to a Normal Human Conjunctive Epithelium Cell Line (IOBA-NHC) Infected with Adenovirus (ADV-5)

Figure 5:
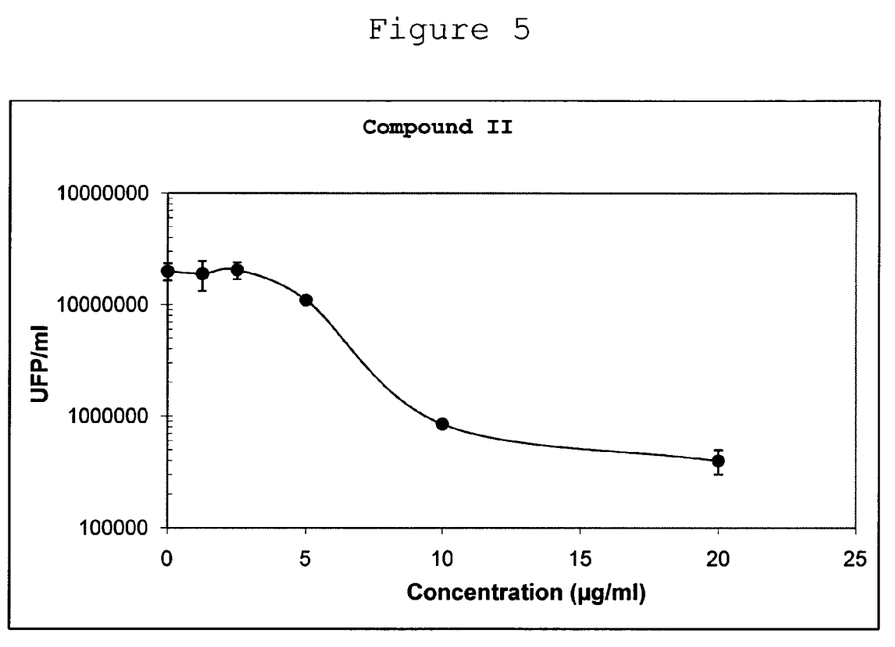
FIG. 5 shows the antiviral activity of compound II according to concentration used against adenovirus in cultures of normal human conjunctive epithelium cell line infected with adenovirus (ADV-5).

The compound II shows antiviral activity against adenovirus. By cultures of a normal human conjunctive epithelium cell line designated IOBA-NHC, infected with adenovirus (ADV-5), at a multiplicity of infection of 1 and treated with different concentrations of compound II, the inventors of this invention have been able to show that said compound inhibits virus replication according to the concentration of compound used (FIG. 5).

The antiviral selectivity index of Compound II for adenovirus is of 15.67 Said index was determined as a quotient between its viral activity (=62.6) and its cytotoxicity (=4).

Figure 6:
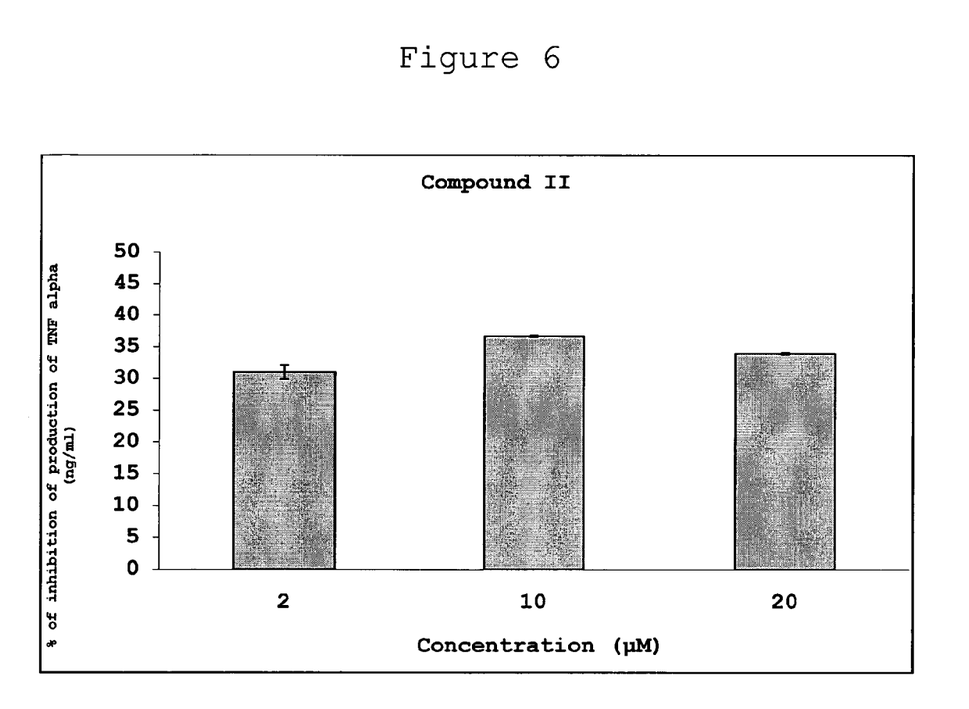
FIG. 6 shows the anti-inflammatory activity of compound II at different concentrations as demonstrated by percentage of inhibition of alpha-TNF production in macrophages.

Also, said compound II has anti-inflammatory activity. By cultures of a cell line of inflammatory cells (macrophages) designated J774, treated with an agent that produces inflammation (LPS) and different concentrations of Compound II, the inventors of this invention have been able to show that said compound inhibits production of alpha-TNF in cultures of macrophages. Data evidencing said conclusion are shown in FIG. 6.

Example 15

Examples of Pharmaceutical Compositions of Ophthalmic use According to the Invention The pharmaceutical compositions of ophthalmic use comprising the compounds of the invention have shown to be effective from a concentration of 2 mg/100 ml. Preferably, the pharmaceutical compositions of ophthalmic use according to the invention can contain from about 10 to about 100 mg/ml.
Ophthalmic Solution that can be Administered in the Form of Drops The examples of ophthalmic solutions to be administered in the form of drops containing one or more compounds of the invention can be those in the form of a sterile aqueous or oily solution, which optionally can contain anti-microbial preservatives, such as benzalkonium chloride. Said solutions may be in the form of monodoses or multidoses. Preferably, those in the form of monodoses will not contain antimicrobial preservatives. Said solutions will have a viscosity of about 3-7 centistokes, a pH of about 5.8 to 7.2 and an osmolarity of about 290 to 310 mosm/kg. The skilled in the art shall be able to select the suitable excipients so that the ophthalmic solution is not toxic or irritating to the conjunctiva and the cornea when instillated on the ocular surface.

Ophthalmic Drops in the Form of Suspension

The examples of ophthalmic suspensions to be administered in the form of drops containing one or more compounds of the invention can be those in the form of a sterile aqueous suspension, which optionally can contain anti-microbial preservatives, such as benzalkonium chloride. Said solutions may be in the form of monodoses or multidoses. Preferably, those in the form of monodoses will not contain antimicrobial preservatives. Preferably, said suspension shall contain Tiloxapol or any similar excipient to allow the compounds of the invention to stay in suspension during an adequate period of time.

The aqueous suspensions containing one or more compounds according to the invention will have a viscosity of about 3-7 centistokes, a pH of about 5.8 to 7.2 and an osmolarity of about 290 to 310 mosm/kg. The skilled in the art shall be able to select the suitable excipients so that the ophthalmic solution is not toxic or irritating to the conjunctiva and the cornea when instillated on the ocular surface.

Ophthalmic Lotions

The ophthalmic lotions containing one or more of the compounds of the invention shall be sterile and may be used for ocular lavages or to impregnate the compounds of the invention on the ocular surface.

The examples of ophthalmic lotions containing one or more compounds of the invention can be those in the form of a sterile aqueous lotion, which optionally can contain antimicrobial preservatives, such as benzalkonium chloride. Said solutions may be in the form of monodoses or multidoses. Preferably, those in the form of monodoses will not contain antimicrobial preservatives. The skilled in the art shall be able to select the suitable excipients so that such ophthalmic preparation is not toxic or irritating to the conjunctiva and the cornea when instillated on the ocular surface.

The aqueous lotions containing one or more compounds according to the invention will have a viscosity of about 3-7 centistokes, a pH of about 5.8 to 7.2 and an osmolarity of about 290 to 310 mosm/kg. The skilled in the art shall be able to select the suitable excipients so that the ophthalmic lotion is not toxic or irritating to the conjunctiva and the cornea when administered on the ocular surface.

Ophthalmic Semisolid Preparations

Semisolid preparations containing one or more compounds according to the present invention will be sterile in the form of ointments, creams or gels, which, will be applied on the conjunctiva. Said preparations may contain one or more soluble substances that attain a homogeneous distribution and aspect. The skilled in the art shall be able to select the suitable excipients so that said ophthalmic preparation is not toxic or irritating to the conjunctiva and the cornea when administered on the ocular surface.

Similar conditions must be taken into consideration in the preparation of ophthalmic inserts and intraocular ophthalmic preparations.

What is claimed is:

1. A method of treatment for herpetic stromal keratitis and epidemic keratoconjunctivitis comprising:
   administering to a patient in need thereof a compound according to formula I:

Formula I wherein $R_1$ and $R_2$ are both HO;
$R_3$ is selected from H, HO and F;
$R_4$ is selected from H, methyl and ethyl; and
⚌ can be a single bond or double bond, with the proviso that when $R_1$ and $R_2$ are both HO, $R_3$ is H, and $R_4$ is ethyl,
⚌ is a single or double bond and the configurations of carbon atoms C22 and C23 respectively linked to the substituents $R_1$ and $R_2$ are S for both carbon atoms.

2. The method according to claim 1, wherein the compound is a compound according to formula IA:

Formula IA wherein the configurations of carbon atoms C22 and C23 respectively linked to the substituents HO are S for both carbon atoms.

3. The method according to claim 1, wherein the compound is a compound according to formula IB:

Formula IB wherein the configurations of carbon atoms C22 and C23 respectively linked to the substituents HO are S for both carbon atoms.

4. The method according to claim 1, wherein the epidemic keratoconjunctivitis is produced by adenovirus.

5. An anti-inflammatory and antiviral compound according to formula I:

Formula I wherein $R_1$ and $R_2$ are both HO
$R_3$ is selected from H, HO and F;
$R_4$ is selected from H, methyl, and ethyl; and
⚌ can be a single or double bond, with the proviso that when $R_1$ and $R_2$ are both HO, $R_3$ is H, and $R_4$ is ethyl,
⚌ is a single or double bond and the configurations of carbon atoms C22 and C23 respectively linked to the substituents $R_1$ and $R_2$ are S for both carbon atoms; and
wherein the compound of formula I is selected from the group of compounds consisting of (22S,23S)-22,23-dihydroxy-6α-fluorostigmast-4-en-3-one, (22S,23S)-22,23-dihydroxy-6α-fluorostigmasta-1,4-dien-3-one, (22S,23S)-6α-22,23-trihydroxystigmast-4-en-3-one, (22S,23S)-6α-22,23-trihydroxystigmasta-1,4-dien-3-one and a compound according to formula IB:

Formula IB wherein the configurations of carbon atoms C22 and C23 respectively linked to the substituents HO are S for both carbon atoms.

6. A pharmaceutical composition, comprising:
a compound according to formula I:

Formula I wherein $R_1$ and $R_2$ are both HO;
$R_3$ is selected from H, HO and F;
$R_4$ is selected from H, methyl, and ethyl; and
⚌ can be a single or double bond, with the proviso that when $R_1$ and $R_2$ are both HO, $R_3$ is H, and $R_4$ is ethyl,
⚌ is a single or double bond and the configurations of carbon atoms C22 and C23 respectively linked to the substituents $R_1$ and $R_2$ are S for both carbon atoms; and
pharmaceutically acceptable excipients.

7. The pharmaceutical composition according to claim 6, wherein the compound is a compound according to formula IA:

Formula IA wherein the configurations of carbon atoms C22 and C23 respectively linked to the substituents HO are S for both carbon atoms.

8. The pharmaceutical composition according to claim 6, wherein the compound is a compound according to formula IB:

Formula IB wherein the configurations of carbon atoms C22 and C23 respectively linked to the substituents HO are S for both carbon atoms.

9. A pharmaceutical composition according to claim 6, wherein the pharmaceutical composition is an ophthalmic pharmaceutical composition.

10. The ophthalmic pharmaceutical composition according to claim 9, wherein the composition is in a liquid form or a semisolid form.

11. The ophthalmic pharmaceutical composition according to claim 10, wherein the liquid form is selected from the group consisting of a solution, a suspension, a lotion, a gel and an intraocular preparation.

12. The ophthalmic pharmaceutical composition according to claim 10, wherein the semisolid form is selected from the group consisting of a formulation, a gel, an insert and an intraocular preparation.

13. An ophthalmic pharmaceutical composition according to claim 10, further comprising:
about 10 to about 100 mg/ml of the compound of formula I, and
wherein the configurations of carbon atoms C22 and C23 respectively linked to the substituents HO are S for both carbon atoms.

* * * * *